(12) United States Patent
Trieu

(10) Patent No.: US 8,100,971 B2
(45) Date of Patent: Jan. 24, 2012

(54) COATINGS FOR SPINAL IMPLANTS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 979 days.

(21) Appl. No.: 11/982,755

(22) Filed: Nov. 5, 2007

(65) Prior Publication Data

US 2009/0118831 A1 May 7, 2009

(51) Int. Cl.
*A61F 2/44* (2006.01)

(52) U.S. Cl. .................. 623/17.11; 623/17.16; 606/246; 606/279; 427/2.26

(58) Field of Classification Search .................... 606/60, 606/61, 246, 278, 279; 623/17.11–17.16; 264/212–218; 427/2.26
See application file for complete search history.

(56) References Cited

U.S. PATENT DOCUMENTS

| | | | |
|---|---|---|---|
| 3,939,049 A | 2/1976 | Ratner et al. | |
| 3,975,350 A | 8/1976 | Hudgin et al. | |
| 3,987,497 A | 10/1976 | Stoy et al. | |
| 4,100,309 A | 7/1978 | Micklus et al. | |
| 5,932,299 A | 8/1999 | Katoot | |
| 6,242,041 B1 | 6/2001 | Katoot et al. | |
| 7,109,255 B2 | 9/2006 | Loomis et al. | |
| 7,655,026 B2 * | 2/2010 | Justis et al. | 606/259 |
| 7,682,540 B2 * | 3/2010 | Boyan et al. | 264/212 |
| 2005/0113919 A1 * | 5/2005 | Cragg et al. | 623/17.11 |
| 2006/0282166 A1 | 12/2006 | Molz et al. | |
| 2007/0179613 A1 | 8/2007 | Heinz | |

FOREIGN PATENT DOCUMENTS

WO 2006116559 A2 11/2006

OTHER PUBLICATIONS

International Search Report and Written Opinion for US Application PCT/US2008/082354 mailed on Jun. 10, 2010.

* cited by examiner

*Primary Examiner* — Eduardo C Robert
*Assistant Examiner* — Christina Negrelli

(57) ABSTRACT

The present application describes a spinal implant device comprising a load-bearing component having at least one soft tissue-facing surface and a coating affixed to the soft tissue-facing surface. The coating is operable to define an interface with the soft tissue that exhibits one or more of the following features: reduced friction, reduced tissue irritation, reduced adhesion, reduced inflammation, reduced incidence of infection and reduced pain, relative to the soft tissue-facing surface in the absence of the coating. Other embodiments include methods of use and manufacture of the apparatus. The application also describes a method involving affixing a load-bearing prosthetic spinal implant device to first and second vertebrae of a motion segment and, after the device is affixed, applying to a soft tissue-facing surface of the device a flowable, curable coating material operable to cure in situ to form a coating.

28 Claims, 5 Drawing Sheets

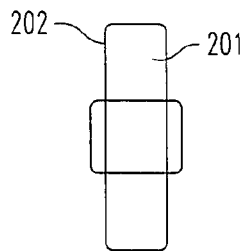 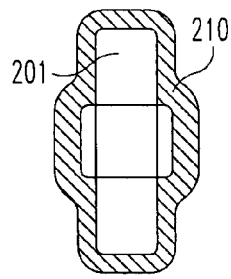 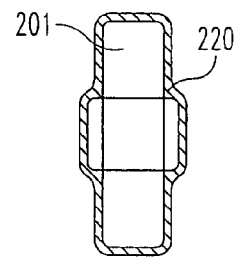
*Fig. 3A*  *Fig. 3B*  *Fig. 3C*
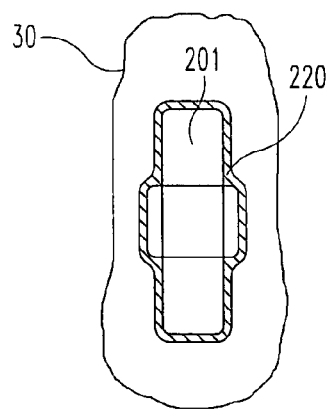
*Fig. 4A*
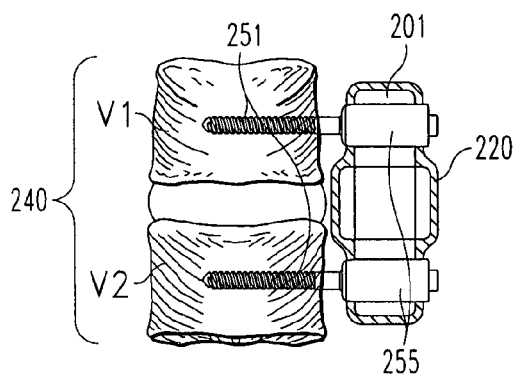  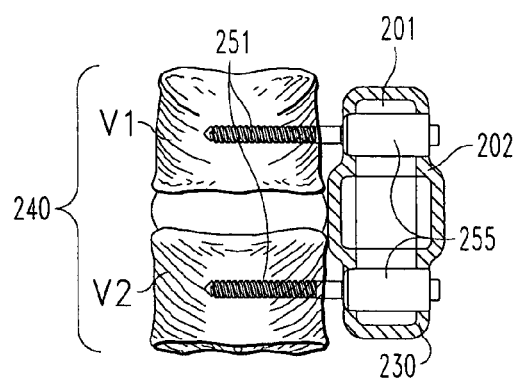
*Fig. 4B*  *Fig. 4C*

COATINGS FOR SPINAL IMPLANTS

BACKGROUND

The present application relates to an orthopedic prosthetic implant device and a manner of using and making the same, and more specifically, but not exclusively, concerns an orthopedic prosthetic implant device having a coating at an interface between the device and host soft tissue.

The use of prosthetic implant devices constructed of plastics, polymers, metals, ceramics or materials made from composites of these materials to address orthopedic injuries and deformities has become commonplace. Such implant devices typically have one or more surfaces that are placed in direct contact with living tissues and some devices include surfaces against which living tissues of the host slide or otherwise move in normal use. In this arena, concerns are sometimes raised about decreasing the invasiveness of the implants and the procedures for implanting them, improving implant integrity, and improving patient outcomes.

Despite the many positive benefits that are gained by the use of such implant devices, contact between the surfaces of the implant and soft tissues of the host, including muscle tissues, blood and the like, can produce unwanted results. For example, dynamic contact between the surfaces of the implant and soft tissue of the host can cause significant abrasive damage to fragile and sensitive human cells and tissues. These dynamic contacts can also cause a wide range of undesirable effects such as tissue and cell adhesion, irritation, inflammation, thrombogenicity (clotting of the blood), hemolysis, bacterial adhesion and infections, unwanted mineral deposits, and increased pain or limited motion, to name a few.

There is still some room for further improvement of such devices, resulting in a need for continued contributions in this technical area.

SUMMARY

The present application provides devices and methods of making and using the devices, whereby the devices include a coating on at least one soft tissue-facing surface. In one embodiment, there is provided a load-bearing spinal implant device and/or a load-bearing component of a spinal implant device having a coating on at least one soft tissue-facing surface. A load-bearing spinal implant device in one embodiment includes a load-bearing component defining at least one soft tissue-facing surface; and a coating affixed to the soft tissue-facing surface, the coating operable for extended contact with soft tissue in vivo; wherein the coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating.

Another embodiment of the present application includes a method for making a spinal implant device having at least one soft tissue-contacting surface that includes: (1) providing a load-bearing spinal implant device having at least one soft tissue-facing surface; and (2) applying to the soft tissue-facing surface a coating operable for extended contact with soft tissue in vivo. The coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating.

Still another embodiment of this application is directed to a method of using a spinal implant device to achieve immobilization or stabilization of a vertebral motion segment. The method includes (1) providing a load-bearing prosthetic spinal implant device including a load-bearing component defining at least one soft tissue-facing surface and a coating affixed to the soft tissue-facing surface, the coating operable for extended contact with soft tissue in vivo; and (2) surgically affixing the device to a first vertebrae and a second vertebrae of the motion segment. The coating is operable to define an interface with the soft tissue that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating.

Another aspect of the application includes a method for achieving immobilization or stabilization of a vertebral motion segment that includes (1) providing a spinal implant device having at least one soft tissue-facing surface; (2) preparing a surgical site by surgically exposing a vertebral motion segment in need of immobilization or stabilization; (3) surgically affixing the device to a first vertebra and a second vertebra of the motion segment; and (4) after said affixing, applying to the soft tissue-facing surface a flowable, curable coating material operable to cure in situ to form a coating effective for extended contact with soft tissue in vivo. The coating is operable to define an interface with the soft tissue that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating.

Further embodiments, forms, features and aspects of the present application shall become apparent from the detailed description and figures provided herewith.

BRIEF DESCRIPTION OF THE DRAWING

FIGS. 3A-3C depict front elevation views of a spinal rod embodiment without a coating thereon and at various stages of applying a coating thereon, with the coating shown in cross section.

FIG. 4A is a front elevation view of a spinal rod embodiment contained in a package.

FIG. 4B is a side elevation view of a spinal rod/screw construct embodiment in an implanted position.

FIG. 4C is a side elevation view of a spinal rod/screw construct embodiment in an implanted position.

DETAILED DESCRIPTION OF SELECTED EMBODIMENTS

Figure 1:
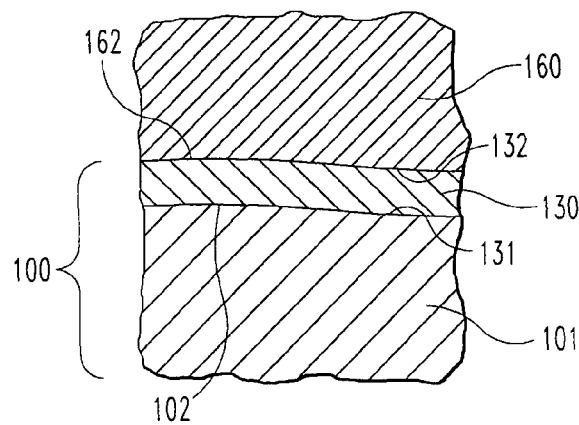
FIG. 1 is a partial cut-away sectional view of a spinal implant device embodiment shown in an implanted position in contact with adjacent soft tissue.

For the purpose of promoting an understanding of the principles of the invention, reference will now be made to the embodiments illustrated in the drawings and specific language will be used to describe the same. The following description is intended to convey a thorough understanding of the present invention by providing a number of specific embodiments and details involving prosthetic spinal implant devices, methods of their manufacture, and methods of their use. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Prosthetic spinal implant devices and components of prosthetic spinal implant devices described herein have at least one soft tissue-facing surface. As used herein, the phrase "soft tissue-facing surface" refers to a surface of an implant device that, after surgical implantation of the device, faces toward soft tissue and, in the absence of a coating as described herein, would be adjacent to and in contact with the soft tissue. The phrase "soft tissue" is used herein to refer to any host tissue other than bone. A person skilled in the art will appreciate that certain implant devices and certain components of implant devices also include bone-contacting surfaces. Bone-contacting surfaces are typically configured to engage adjacent bone for rigidly or dynamically affixing the device and/or component of the device to a bone. Relatively high frictional values are typically desired between the bone and the bone-contacting surfaces of some devices, such as, for example, bone screws and bone anchors, to achieve an effective load-bearing connection between the bone and the device. In certain embodiments, coatings are not applied to bone-contacting surfaces of the device or bone-contacting surfaces of components of the device. In other embodiments, coatings are applied to bone-contacting surfaces in addition to soft tissue-facing surfaces. For example, for ease of manufacture, a bone-contacting surface of a bone plate can include the coating without producing undesirable results. Similarly, a person skilled in the art will appreciate that some prosthetic spinal implant devices include multiple components that are affixed to one another before or during the surgical implantation process by, for example, screws, brackets, clamps and other attachment devices. In certain embodiments, the coatings are not applied to component-contacting surfaces of an implant component. In other embodiments, coatings are applied to component-contacting surfaces in addition to soft tissue-facing surfaces.

With reference to FIG. 1, a portion of a prosthetic spinal implant device 100 is shown in cross section. In FIG. 1, load-bearing component 101 includes a soft-tissue facing surface 102 that faces toward soft tissue 160. Coating 130 is positioned between surface 102 of load-bearing component 101 and surface 162 of soft tissue 160. Coating 130 has an implant-contacting surface 131 and a soft tissue-facing surface 132. Surface 132 of coating 130 and surface 162 of soft tissue 160 form an interface between device 100 and soft tissue 160 and, in some embodiments, surfaces 132 and 162 will move relative to one another in ordinary use. Due to the properties of coating 130, the interface between surface 132 of coating 130 and surface 162 of soft tissue 160 exhibits one or more of reduced friction, reduced tissue irritation, reduced adhesion, reduced inflammation, reduced incidence of infection and reduced pain, relative to an interface that would occur between surface 162 of soft tissue 160 and soft tissue-facing surface 102 of load-bearing component 101 if coating 130 were absent. Inclusion of coating 130 over component 101 provides a device exhibiting one or more desirable features, such as, for example and without limitation, one or more of the following features: improved compatibility with host tissues, reduced friction between implant and host soft tissue, reduced tissue irritation, reduce tissue adhesion, reduced tissue damage, reduced inflammation, reduced incidence of infection, reduced pain, reduced fibrous capsule formation, reduced difficulty of implant removal, improved implant performance and/or increased implant service life. In one preferred embodiment, coating 130 is a lubricious coating.

The terminology used herein is for the purpose of describing particular embodiments only and is not intended to limit the scope of the present application. Throughout this description, the expressions "spinal implant device" or "spinal implant device component" are used to denote any man-made implant material or component thereof that is used to provide partial or full load-bearing support for the spinal column and that includes at least one soft tissue-facing surface. Man-made prosthetic spinal implant devices can be made using a wide range of materials such as polymeric materials, metals and ceramics. Examples of polymeric materials include, but are not limited to, thermoplastic polymers, thermoset polymers, elastomers, adhesives, sealants, and composites thereof. Examples of metals include medical grade stainless steel, titanium and titanium alloy. Examples of ceramics include pyrolytic carbon, carbon fibers, zirconia, lumina, titania, and the like.

Spinal implant devices and spinal implant device components contemplated by this application that include a coating over one or more soft tissue-facing surfaces include any component that is intended to contact a soft tissue of a host, may be in a wide variety of shapes and sizes, and may be constructed to operate in a wide variety of ways, including but not limited to the commonly-known forms useful as rods, plates, interspinous process devices, prosthetic disc nucleus and disc prostheses, and constructs including same. Other components that may be coated as described herein include bone screws, bone anchors, brackets or other components used to attach other load-bearing components to adjacent vertebral bodies or other bony portions, or to other components, and also may comprise supporting bands or outer sheaths, bags, jackets, balloon, bands, tethers, cables, cords and the like. A wide variety of the spinal implant devices, or components thereof, can be modified as described herein by applying to at least one soft tissue-facing surface thereof a coating as described herein.

The coating can be comprised of a wide variety of materials or combinations of materials that are operable to reduce friction or otherwise enhance the relative motion between the implant device and the adjacent soft tissue, that reduce tissue irritation, that reduce adhesion, that reduce inflammation, that reduce incidence of infection and/or that reduce pain. Alternatively, the coating can be comprised of a material or combination of materials that can be made to undergo a transformation from a first form to a second form (e.g., by hydration upon application of water, by application of heat or light, by curing, or by other manner of initiating a transformation) that reduces friction, or otherwise enhances the relative motion between the implant device and the adjacent soft tissue, reduces tissue irritation, reduces adhesion, reduces inflammation, reduces incidence of infection and/or reduces pain. For example, the coating may be comprised of a hydrogel material that can be transformed from a first dehydrated form to a second hydrated form upon application of water. Alternatively, in some embodiments described herein, the coating may be comprised of a curable-type composition that initially has flowable, malleable or otherwise deformable characteristics, but that cures or transforms upon application of fluid, time, heat, light or other curing means, to form a coating after implantation. In one embodiment, the coating is adhered to the soft tissue-facing surface of a spinal implant device or a component thereof. For example and without limitation, the coating can be adhered to the implant surface via chemical means, by ionic bonding, by physical attachment or combinations thereof.

In one embodiment, the coating is a hydrogel or xerogel material. Exemplary hydrogel materials that can be used to form the coating include, without limitation, a polyvinyl alcohol, a polyacrylic acid, a polyarylamide, a poly(acrylonitrile-acrylic acid), a polyurethane, a polyethylene glycol, a poly (N-vinyl-2-pyrrolidone), a gelatin, a collagen, a polysaccharide, a cellulose, and combinations thereof. In one embodiment, the hydrogel coating exhibits a water content when fully hydrated of at least 25% by weight. In another embodiment, the hydrogel coating exhibits a water content when fully hydrated of at least 50% by weight.

In embodiments in which the coating is a hydrogel and curing of the hydrogel requires activation of a crosslinking agent, the crosslinking agent can be activated in both humid and non-humid environments. In some instances, it is preferred that the activation take place in a humid environment. In these cases, the hydrogel is formed directly. In one manner of making a hydrogel coating by crosslinking in a humid environment, the humid environment contains from about 20% to about 100% water. In another embodiment, the humid environment contains from about 60% to about 100% water. In cases where the crosslinking is effected in non-humid environments, a xerogel is formed, which can be converted to a hydrogel upon subsequent exposure of the crosslinked xerogel to a humid environment.

In some circumstances in which a spinal implant is used, the coating will desirably be of a type that is permanent. As used herein, the term "permanent" refers to a coating that is sufficiently stable in vivo that it will remain positioned on the tissue-facing surface without substantial degradation after the implant is implanted into a patient. In such an embodiment, the hydrogel selected for use in the coating is one that is nonbiodegradable. Nonbiodegradable hydrogels are available commercially, and examples include, without limitation, a crosslinked polyvinyl alcohol hydrogel, a crosslinked polyacrylic acid, a polyarylamide, a crosslinked poly(acrylonitrile-acrylic acid), a crosslinked polyurethane and combinations thereof. Alternatively, in other circumstance, the coating will desirably be of a type that is temporary. As used herein, the term "temporary" is used to refer to a coating that remains positioned on the tissue-facing surface for a period of time after the implant is implanted into a patient, and then begins to degrade and be absorbed over time. In such an embodiment, the hydrogel selected for use is biodegradable and bioresorbable. Biodegradable, bioresorbable hydrogels are available commercially, and examples include, without limitation, a gelatin, a collagen, a polysaccharide, a cellulose, a polyethylene glycol, a lightly crosslinked poly(N-vinyl-2-pyrrolidone), a lightly crosslinked polyvinyl alcohol hydrogel, a lightly crosslinked polyacrylic acid, and combinations thereof.

In yet another embodiment, the coating is partially resorbable. For example, in one embodiment a multi-layer coating is applied to a soft tissue-facing surface of a device or component to provide a device having surface properties that change over time after implant. In one embodiment, a nonbiodegradable sub-layer is positioned adjacent the tissue-facing surface of a device or component, and then a biodegradable, bioabsorbable outer layer is positioned adjacent the sub-layer. In such an embodiment, the outer layer is temporary and the sub-layer is permanent. A person skilled in the art will appreciate that different properties can be exhibited by the sub-layer and the outer layer of the coating by selection of materials to be included therein. For example, the biodegradable, bioresorbable outer layer can be formed to have a different degree of lubricity than the sub-layer, and the outer layer can be formed to include therapeutic agents (as described more fully below) that facilitate healing after the implant is surgically implanted. The therapeutic agents can be of a type that diffuse from the outer layer over time after implant, of a type that are released as the outer layer is biodegraded and absorbed after implant, or a combination thereof. The present application also contemplates embodiments in which the coating includes more than two layers. Implants having coatings with more than two layers can be formed to exhibit more complex degradation characteristics and therapeutic agent release characteristics. For example, the various layers of the coating can be formed to be biodegraded and bioresorbed chronologically in a controlled fashion. A multi-layer coating can be formed to be partially resorbable, i.e., to include a sub-layer that is made of a nonbiodegradable material, or can be formed to be fully resorbable, i.e., to include multiple layers, each of which, including the sub-layer, is formed of a biodegradable, bioresorbable material.

Another manner of providing a partially resorbable coating is to provide a coating that is composed of a mixture of materials, one or more of which is biodegradable and bioresorbable, and one or more of which is nonbiodegradable. In such an embodiment, the nonbiodegradable materials will form a matrix in which the biodegradable and bioresorbable materials are contained. Over time after implant of a device of this embodiment, the biodegradable, bioresorbable materials will be degraded and resorbed by the patient, leaving the nonbiodegradable matrix in place permanently.

Figure 2A:
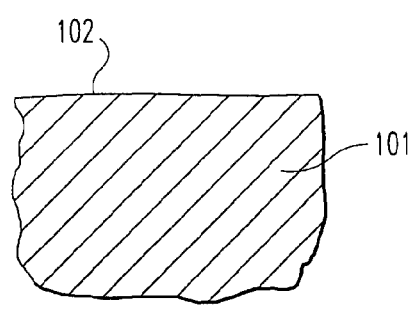
FIGS. 2A-2D are partial cut-away sectional views of a load-bearing component of a spinal implant device without a coating thereon and at various stages of applying a coating thereon.

With reference to FIGS. 2A-2D, a hydrogel coating can be applied to a surface of a load-bearing device component by first applying a hydrogel solution to the surface, then drying or curing the solution to form a dehydrated hydrogel (or xerogel) coating, which can then be packaged, stored and/or shipped for subsequent hydration and use. FIG. 2A depicts load-bearing component 101 with an uncoated soft tissue-facing surface 102. The spinal implant device and/or component to have a coating applied thereto, such as component 101, can be made using techniques known in the art. At least one soft tissue-facing surface of the device or component (i.e., a surface of the device that is intended to ultimately contact soft tissue), such as surface 102 then is coated with a coating. Prior to coating, the soft tissue-facing surface can optionally be pre-treated, such as, for example, with an etching solution, or by a surface roughening technique, as is well known in the art.

Figure 2B:
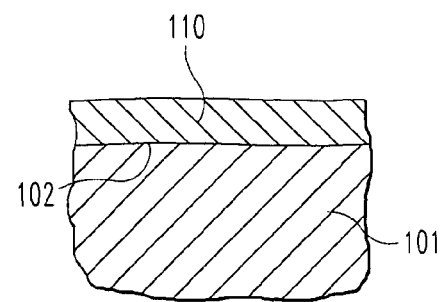
Figure 2C:
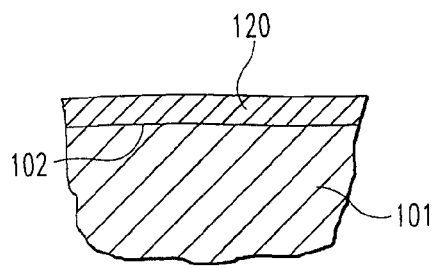

Coating of soft tissue-facing surface 102 can be accomplished using a variety of coating techniques, including but not limited to, spray coating; extrusion coating; plasma sputtering; chemical vapor deposition; injection of materials and curing by applying energy, such as, for example, application of light, heat or chemical energy; injection of one-phase or two-phase self-curing materials; growth of organic layer, and the like. In one manner of applying a coating to surface 102, a hydrogel solution is applied to surface 102, for example by dip-coating or spray-coating, to provide hydrogel solution layer 110 over surface 102 of component 101, as shown in FIG. 2B. Hydrogel solution layer 110 is then dried and/or cured to provide coating 120 over surface 102 of component 101, as depicted in FIG. 2C. Component 101, with dried and/or cured hydrogel coating 120 positioned therein, can be packaged and sterilized for shipment and/or storage, and future implantation into a patient. Improved adhesion or stability of the coating may be obtained by proper surface treatments of the substrate surface before coating. Examples or such treatments include coating with a primer, plasma treatment, suface oxidation, acid etching, electrochemical treatment, texturing, grit blasting and the like.

Figure 2D:
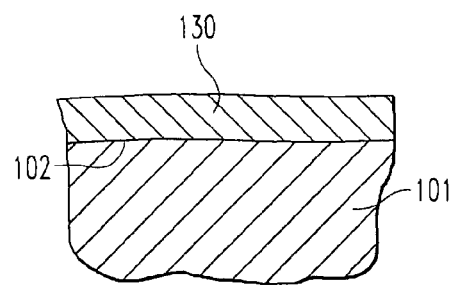

At the time of use, the component is removed from its packaging and the coating is hydrated, either before, during or after affixation of the component to a patient's vertebrae or to another component of an implant. For example, hydration of the coating can be achieved by soaking the coating in a bath of water or other aqueous fluid, such as, for example, saline, blood, blood plasma or the like, prior to implantation for a period of time effective to cause the coating to become hydrated by absorption of water from the soaking bath. Alternatively, hydration can be initiated prior to implantation by contacting the coating to water or other aqueous fluid for a shorter period of time to initiate hydration but not fully hydrate the coating, with further hydration occurring in vivo after implantation. Further hydration after implantation can occur, for example, by introducing an aqueous fluid into contact with the coating in the surgical site after implantation but prior to closing the surgical site, or by absorption of water from the patient's blood or other bodily fluids in vivo after the surgical site is closed. As still another alternative, the component can be implanted in an unhydrated state, with hydration occurring after implantation, either by application of an aqueous hydrating fluid to the coating in vivo prior to closing the surgical site or by absorption of water from the patient in vivo after the surgical site is closed. It is therefore seen that hydration can be completed prior to closing the surgical site, if desired, or can be allowed to proceed to completion after closing the surgical site, if desired. As used herein, the term "completion" and the terms "fully hydrated" are used in connection with hydration of a hydrogel coating to refer to an equilibrium state of hydration achieved by the device in vivo, whether or not this equilibrium state is equivalent to the maximum water loading achievable by the hydrogel. FIG. 2D depicts component 101 having a hydrated hydrogel coating 130 over surface 102. In this hydrated form, coating 130 is a lubricious coating and provides an excellent interface between surface 102 of load-bearing device component 101 and adjacent soft tissue 160 (as depicted in FIG. 1).

In one embodiment, coating 130 has a thickness of from about 1 to about 500 microns. In another embodiment, coating 130 has a thickness of from about 10 to about 250 microns. While multiple embodiments are described herein in which the coating is a hydrogel, it is to be understood that embodiments with hydrogel coatings are described as examples only, and it is not intended that the present application be limited to hydrogel coatings, it being understood that a variety of other materials can be used that operate to define an interface with the soft tissue that exhibits lower friction relative to an interface between the soft tissue and the soft tissue-facing surface of the load-bearing component or achieve one or more other advantageous results as described herein. For example and without limitation, in other embodiments, coating 130 can be composed of a polytetrafluoroethylene-based material, a hydrophobic material, a glassy amorphous material or combinations thereof.

In yet another manner of making a spinal implant device or component having a coating thereon, the coating is first formed as a sheet-like layer and then adhered to a soft tissue-facing surface of a spinal implant device or component. For example, a polymer composition used to form a coating can be spread over a temporary substrate and then crosslinked in a sheet-like form prior to being introduced onto the medical device. Optionally, an adhesive composition can be spread over the coating layer prior to applying the coating to the device or component.

FIGS. 3A-3C depict various stages of making a spinal rod having a coating thereon. In one embodiment rod 201 may be solid but in other embodiments it may be hollow like a tube, may be multi-layered with different layers having different compositional make-up, or may have other features. FIG. 3A depicts spinal rod 201 with an uncoated surface 202. In one manner of applying a coating to surface 202, a hydrogel solution is applied to surface 202, for example by dip-coating or spray-coating, to provide hydrogel solution layer 210 over surface 202 of spinal rod 201, as shown in FIG. 3B. Hydrogel solution layer 210 is then dried and/or cured to provide coating 220 over surface 202 of spinal rod 201, as depicted in FIG. 3C. Spinal rod 201 can have one more apertures (not shown) passing therethrough for receiving screws or other bone attachment devices to attach spinal rod 201 to vertebrae, or can include other surface features for engagement with bone attachment devices. Alternatively, spinal rod 201 can be one component of an implant device that includes other components, such as, for example, brackets, for connecting spinal rod 201 to bone anchors, bone screws or the like. In such an embodiment, portions of surface 202 can optionally be kept uncovered by coating 220, such as, for example, portions that will be in contact with other device components rather than facing soft tissue of the host. Spinal rod 201, with dried and/or cured hydrogel coating 220 affixed thereto, can be packaged and sterilized for shipment and/or storage, and future implantation into a patient.

FIG. 4A depicts spinal rod 201 with dried coating 220 as shown in FIG. 3C in package 30. Spinal rod 201 and package 30 can optionally be sterilized, and can be shipped and/or stored for subsequent use. The hydrogel coatings can be packaged and stored in a variety of ways. For example, the hydrogel can be maintained in a hydrated state for an extended period of time. Alternatively, as depicted in FIG. 4A, the hydrogel can be dehydrated and stored in an essentially desiccated state until use, since the hydration and dehydration of the hydrogel coating is completely reversible. Furthermore, plasticizers can be added to the dehydrated materials to provide materials with increased flexibility. Plasticizers useful in this application include, but are not limited to, glycerol, propylene glycol, and triethyl citrate.

At the time spinal rod 201 is to be implanted into a patient, rod 201 can be removed from package 30 and affixed to first and second vertebrae V1, V2 of spinal motion segment 240 as depicted in FIG. 4B using bone screws 251. At the time of use, spinal rod 201 is removed from packaging 30 and the coating is hydrated, either before, during or after affixation of rod 201 to vertebrae V1, V2. For example, hydration of coating 220 can be achieved by soaking coating 220 in a bath of water or other aqueous fluid, such as, for example, saline, blood, blood plasma or the like, for a period of time sufficient to fully hydrate coating 220 by absorption of water from the soaking bath prior to affixation to vertebrae V1, V2. Alternatively, hydration can be initiated prior to implantation by contacting coating 220 to water or other aqueous fluid, with further hydration occurring in vivo after affixation of rod 201 to vertebrae V1, V2. The hydration process can be completed by introducing an aqueous fluid into contact with the coating in the surgical site after implantation but prior to closing the surgical site, or by absorption of water from the patient's blood or other bodily fluids in vivo after the surgical site is closed. As still another alternative, as depicted schematically in FIG. 4B, rod 201 with unhydrated coating 220 thereon is affixed to vertebrae V1, V2 in an unhydrated state, with hydration occurring after affixation of rod 201 to vertebrae V1, V2, either by application of an aqueous hydrating fluid to coating 220 in vivo or by absorption of water from the patient in vivo. In the assembly depicted in FIG. 4B, rod 201 is affixed to bone screws 251 by attachment members 255, which are represented schematically in FIG. 4B. Attachment members 255 can take a wide variety of forms, many examples of which are described in the prior art, and contemplated by the present application. Alternatively, bone screws 251 and attachment members can be integrated into a single bone attachment device (not shown) for rigidly attaching rod 201 to vertebrae V1, V2, a variety of examples of which are described in the prior art. For example, and without limitation, the bone attachment device can be a multiaxial bone screw assembly (not shown) that includes a multiaxial bone screw and a head. The head can alternatively be referred to as a saddle member. The multiaxial bone screw and the head attach to one another in a manner to allow a range of motion in one, several, or all directions facilitating easier interconnection of system components. The multiaxial bone screw includes a longitudinal threaded stem structured to engage a bony surface. The head includes a socket, socket threading, a channel, and upright portions, all configured to receive and attach the bone screw to rod 201. It is not intended that the present application be limited to the described bone attachment device, it being understood that a wide variety of alternatives are know to persons of ordinary skill in the art. Hydration of coating 230 can be completed prior to closing the surgical site, if desired, or can be allowed to proceed to completion after closing the surgical site, if desired. FIG. 4C is a schematic depiction of rod 201 having a hydrated hydrogel coating 230 over surface 202. In this hydrated form, coating 230 is a lubricious coating and provides an excellent interface between surface 202 of rod 201 and adjacent soft tissue (not shown).

Figure 5:
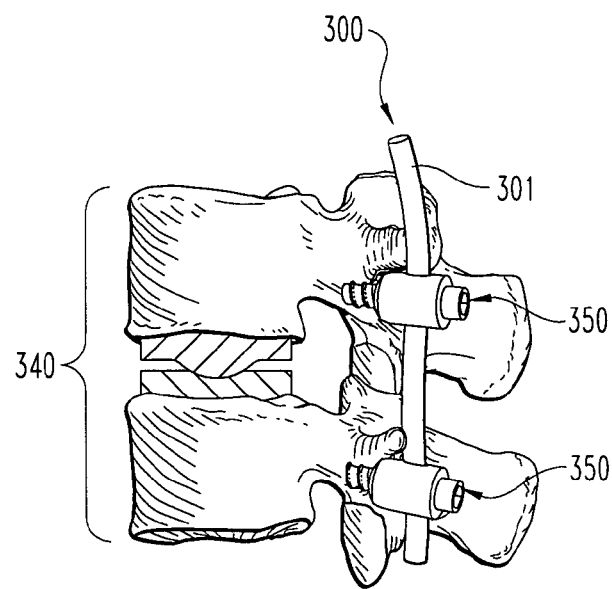
FIG. 5 is a side elevation view of a spinal rod/screw construct embodiment in an implanted position.

FIG. 5 illustrates a spinal rod assembly 300 in its implanted configuration, i.e., affixed to motion segment 340 of a spinal column of a patient, and having a coating thereon. Assembly 300 generally includes two bone attachment devices 350 and a rod 301 structured to interconnect with the bone attachment devices 350. In a preferred embodiment, each of bone attachment devices 350 is a multiaxial bone screw assembly. Bone attachment devices 350 may be affixed to various locations of the spinal column wherein subsequent insertion of rod 301 may be utilized to fix different areas of the spinal column relative to one another in an effort to promote healing of various spinal deformities. Posterior fixation system 300 may be used for, but is not limited to, treatment of degenerative spondylolisthesis with objective evidence of neurologic impairment, fracture, dislocation, scoliosis, kyphosis, spinal tumor, and/or a failed previous fusion. Soft tissue-facing surfaces of rod 301 and bone attachment devices 350 have a coating thereon.

Figure 6:
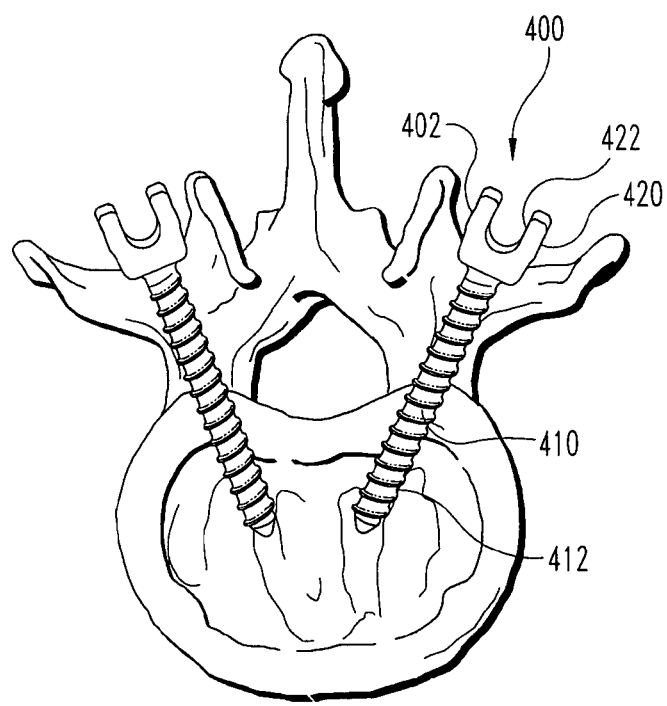
FIG. 6 is a top view of a bone attachment device embodiment in an implanted position in a vertebra, with a cut-away view of the vertebra shown.

FIG. 6. depicts an embodiment of the present application in which the load-bearing member to which a coating is applied is bone attachment device 400, shown in context of an anterior cross-sectional view of vertebra V. Bone attachment device 400 is a bone screw assembly that includes longitudinal threaded stem 410 and head 420. Stem 410 and head 420 can be attached to one another in a manner to allow a range of motion in one, several, or all directions facilitating easier interconnection of other system components (not shown) or can be rigidly attached to one another. Threaded stem 410 is structured to engage a bony surface. When coating a soft-tissue-facing surface of a component, it is sometimes desirable to avoid coating other surfaces of the component that are not tissue-facing. As one representative example, bone attachment device 400 includes soft tissue-facing surface 402 and also non-soft-tissue-facing surfaces that are configured to engage bone, such as, for example, surface 412 of stem 410, and/or that are configured for connection to other device components, such as, for example, inner surface 422 of head 420. In the embodiment shown, soft tissue-facing surfaces of head 420 have a coating thereon and surfaces 412 and 422 do not have a coating thereon.

Figure 7:
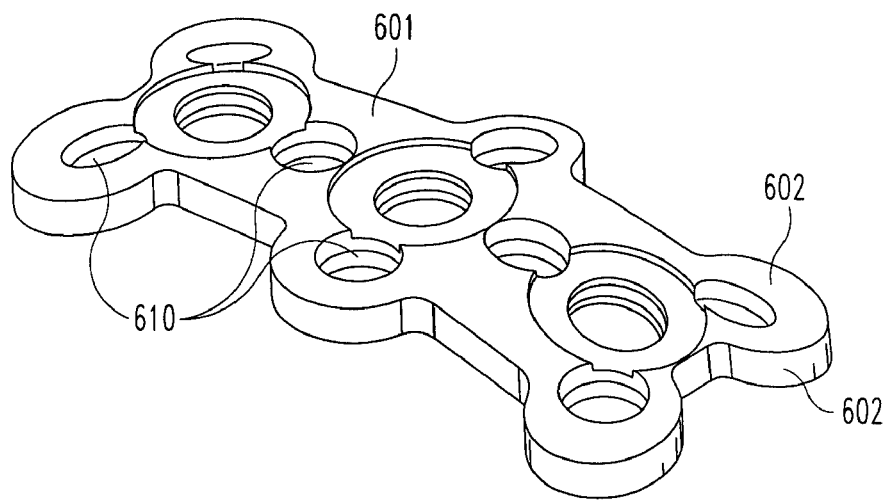
FIG. 7 is a perspective view of a bone plate embodiment.

Another example of a device component that includes a soft-tissue-facing surface and also non-tissue-facing surfaces is bone plate 601 depicted in FIG. 7. Bone plate 601 includes soft tissue-facing surfaces 602 and non-soft-tissue-facing surfaces (not shown). For example, bone plate 601 includes a lower surface (not shown) that is configured to face bony portions of a spinal column (not shown) when plate 601 is implanted into a patient. In addition, plate 601 includes surfaces that are configured for connection to other components. For example, bone plate 601 defines apertures 610 that are configured to receive bone screws or other bone attachment devices when plate 601 is affixed to a patient's spinal column and to engage such bone screws or other attachment devices. Such surfaces of plate 601, which do not face soft tissue of a host when plate 601 is in an implanted position, can optionally include a coating or can be devoid of a coating; however, at least one of soft tissue-facing surfaces 602 has a coating thereon as described herein.

To make a spinal implant device having a coating over some, but not all, surfaces of the device (i.e., having a coating over soft tissue-facing surfaces but not bone-contacting surfaces) a variety of techniques can be employed. For example, in one manner of achieving this result, non-soft-tissue-facing surfaces of the device or component can be temporarily covered before the coating material is applied to the soft tissue-facing surface. The temporary covering can then be removed after the coating is dried and/or cured, or after a sufficient degree of drying and/or curing is achieved. For example, with regard to apertures in a bone plate, such apertures can be temporarily plugged during application of the coating and during drying and/or curing operations, and then the plug can be removed before packaging or immediately prior to use of the device. Alternatively, in some embodiments, the coating can be applied to the entire device, and then the coating material can be removed from non-soft-tissue-facing surfaces before packaging, for example, by suitable mechanical or chemical means. As yet another alternative, when a device is made by first providing a coating in a sheet-like layer and then adhering the layer to one or more soft tissue-facing surfaces of the device, the coating can be applied to some, but not all, surfaces of the device by first shaping the coating layer to correspond to the surfaces desired to be covered, and then applying the shaped layer to the selected soft tissue-facing surfaces of the device.

Figure 8:
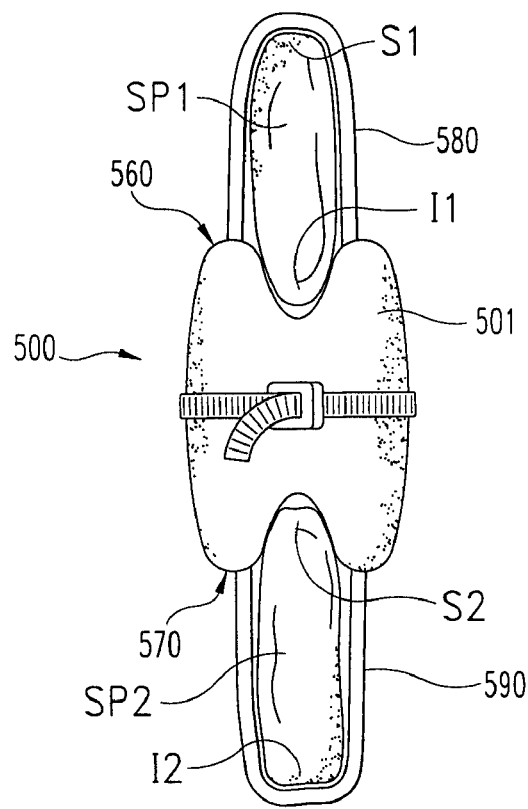
FIG. 8 is a side elevation view of a dynamic interspinous process device in an implanted position.

In another embodiment, depicted in FIG. 8, inter-spinous dynamic fixation device 500 includes a coating over soft tissue-facing surfaces. In FIG. 8, inter-spinous dynamic fixation device 500 is shown in the context of upper spinous process SP1 of an upper vertebra of a spinal motion segment and lower spinous process SP2 of a lower vertebra of the spinal motion segment. The upper and lower vertebrae and disc therebetween (not shown) comprise a spinal motion segment, it being understood that a spinal motion segment may alternatively include multiple vertebral levels. Upper spinous process SP1 extends from an upper lamina (not shown) of upper vertebra and lower spinous process SP2 extends from a lower lamina (not shown) of lower vertebra. The spinous processes SP1, SP2 and laminae comprise posterior elements of the vertebrae of the spinal motion segment.

Spinal implant device 500 includes spacer member 501 positioned in engagement with the posterior vertebral elements to provide dynamic spinal stabilization. Spacer member 501 extends between and contacts adjacent surfaces of spinous processes SP1, SP2 to limit movement of the spinous processes toward one another as a result of extension of the spinal motion segment. For example, spacer member 501 includes upper end 560 in contact with inferior side I1 of spinous process SP1, and lower end 570 in contact with superior surface S2 of spinous process SP2. Spacer member 501 can include a body structured to resiliently compress in response to extension of the spinal motion segment, providing resistance to the extension forces and limiting movement of the spinous processes SP1, SP2 toward one another as spacer member 501 is compressed. Implant device 500 can be affixed to upper vertebra and lower vertebra in any suitable manner, many alternatives of which are known in the art, and a few of which are discussed herein.

Spacer member 501 can be fabricated from one or more components that are flexible or exhibit at least some flexibility, and can be manufactured of a uniform composition, or can be formed using multiple diverse materials. Examples of such components include woven fabric tubing, woven and non-woven mesh, or braided or woven structures, sutures, tethers, cords, planar members, bands, wires, cables, or any other component capable of extending between and supporting the adjacent spinous processes SP1, SP2. In certain preferred embodiments, spacer member 501 is fabricated from one or more components that are elastic, and is itself elastic, so it can assume various shapes during and after insertion and attachment. As used herein, the term "elastic" refers to a physical characteristic of a material whereby it is capable of being compressed, stretched or twisted, and capable of resuming its original shape after being compressed, stretched or twisted. It is of course understood that spacer member 501 would be formed of one or more compressible materials where it is desired for device 500 to be used in an application where it is desirable for spacer member 501 to be compressible. Spacer member 501 can include an internal structural component contained within an outer sheath. For example, spacer member 501 can include an inner structural component comprising silicone, which is wrapped in an outer sheath that comprises polyester fabric.

Device 500 can also optionally include an upper engaging member 580 and a lower engaging member 590 extending from spacer member 501. Upper engaging member 580 preferably extends along and contacts superior surface S1 of spinous process SP1, and lower engaging member 590 extends along and contacts inferior surface I2 of spinous process SP2. Engaging members 580, 590, which are preferably tethers, such as cables or straps, are thus operable together to limit movement of spinous processes SP1, SP2 away from one another as a result of flexion of the motion segment. In another embodiment, upper engaging member 580 extends along and contacts a superior surface of the upper lamina (not shown) of the upper vertebra, and lower engaging member 590 extends along and contacts an inferior surface of the lower lamina (not shown) of the lower vertebra. Engaging members 580, 590 can be movably coupled with spacer member 501 to facilitate manipulation of the engaging members 580, 590 and placement over spinous processes SP1, SP2 or the spinal laminae. Various forms for engaging members 580, 590 are contemplated, including cables, wires, sutures, cords, bands, belts, rigid links or rods, and flexible links or rods, for example.

In another embodiment (not shown) an inter-transverse process dynamic stabilization device can have a configuration similar to that described above in connection with inter-spinous process dynamic stabilization device 500, but sized and shaped for placement between transverse processes of adjacent vertebrae rather than between spinous processes of adjacent vertebrae. In this embodiment, the spacer member extends between and contacts adjacent surfaces of the transverse processes to limit movement of the transverse processes toward one another as a result of extension of the spinal motion segment. For example, the spacer member can include an upper end in contact with the inferior surface of the transverse process of the upper vertebra, and a lower end in contact with the superior surface of the transverse process of the lower vertebra. A second inter-transverse process spinal stabilization device can be positioned on the opposite side of the central axis of the spinal column. The second spacer member can be structured like the first and positioned similarly relative to the transverse processes on the opposite side of the central axis. With two spacers positioned as described, the implants work bi-laterally to provide bi-lateral stabilization of the spinal column segment. Additional implants may be provided at one or more additional vertebral levels for multi-level stabilization procedures. It is further contemplated that the implants may be employed to uni-laterally stabilize one or more vertebral levels. The spinal implants, either alone or in combination, can function to distract the spinal space and/or the spinal foramen to relieve nerve root pressure, decompress spinal elements or the like. The implants provide overall stability while maintaining motion capabilities of the spinal motion segment.

In one embodiment, the entire surface of an inter-spinous process dynamic stabilization device or an inter-transverse process dynamic stabilization device is coated with a coating as described herein. In another embodiment, only portions of the surfaces of such devices are coated such as, for example, all surfaces other than the bone-contacting portions of ends 560, 570. In yet another embodiment only the posterior and lateral surfaces of spacer member 501 are coated with a coating. In embodiments in which load-bearing device or component is flexible or deformable, as in the case of spacer member 501, the coating is composed of a material that is also deformable. The present application also contemplates that the coating of such an embodiment can be adhered to the surface of the device or component or, alternatively, can be formed to slide relative to the surface of the device or component. In an embodiment in which the coating and the surface of the device or component can slide relative to one another, the coating operates to provide a lubricious barrier between the device or component and the adjacent soft tissue, while also allowing motion of the deformable implant during normal operation after implant thereof into a patient.

In another manner of implanting a load-bearing spinal implant device having a coating thereon, the load-bearing device, or one or more components thereof, is fixed to one or more bony portions of the spinal column before the coating is applied to one or more soft tissue-facing surfaces of the device or component. For example, a vertebral motion segment can be immobilized or stabilized by affixing a spinal implant device to upper and lower vertebrae of the motion segment, and then applying a flowable, curable coating material to at least one soft tissue-facing surface of the implant, the material being operable to cure in situ to form a coating. This can be accomplished, for example, by surgically exposing a vertebral motion segment in need of immobilization or stabilization, surgically affixing a load-bearing prosthetic spinal implant device defining at least one soft tissue-facing surface to a first vertebrae and a second vertebrae of the motion segment and, after the device is affixed to the vertebrae, applying to the soft tissue-facing surface a flowable, curable coating material that is operable to cure in situ to form a coating. In one embodiment, the flowable, curable material is a biocompatible material that is operable to undergo a phase transition from a flowable/malleable condition to a non-flowable/non-malleable condition. The transition can result from, for example, a physical change such as gellation or a chemical change such as crosslinking, and can be initiated by a variety of means including, for example, application of electromagnetic radiation or chemical energy. Examples of materials that can be used include, without limitation, silicone, polyurethane, epoxy, polymethylmethacrylate, cyanoacrylate, polyvinyl alcohol hydrogel and polyethylene glycol.

Figure 9:
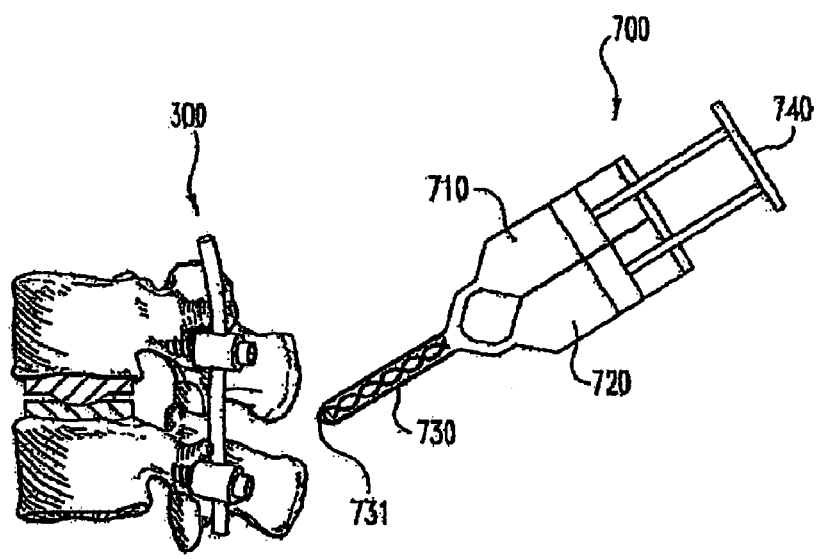
FIG. 9 is a side elevation view of a spinal rod/screw construct embodiment in an implanted position and a side elevation view of a material delivery device.

For example, with reference to FIG. 9, posterior spinal rod/screw construct 300 is implanted surgically using methods known in the art. For example, rod/screw construct 300 can be implanted to support the fusion of an L5-S1 level vertebral motion segment. A two-part self-curing mixture, such as, for example, a two-part, self-curing silicone material, a two-part, self-curing polyvinyl alcohol hydrogel or a two-part, self-curing polyurethane material is then delivered to construct 300 by delivery device 700. Delivery device 700 in the embodiment shown in FIG. 9 is a static mixer operable to mix the materials of a two-part, self-curing material and deliver the mixture to a desired location. In this embodiment, the mixture is delivered onto soft tissue-facing surfaces of construct 300. In particularly preferred embodiments, the self-curing mixture is positioned to cover all screw/rod interfaces and sharp edges of construct 300. The self-curing mixture is then cured to form a coating, such as, for example, an elastomeric layer, before closing the surgical site. In the embodiment shown in FIG. 9, delivery device 700 is a static mixer that includes first and second chambers 710, 720 in which the separate parts of the two-part self-curing mixture are contained up to the time of mixing and delivery. When construct 300 is in position, the two parts can be mixed and delivered to the desired surface or surfaces of construct 300 by pressing plunger 740, thereby applying pressure to the materials positioned in chambers 710 and 720, forcing the materials into contact with one another in mixing conduit 730. Mixing conduit can be, for example, a helical conduit operable to achieve thorough mixing of the separate parts of the two-part mixture, or can have a variety of other configurations operable to achieve mixing, many examples of which are known in the art.

As the materials pass through helical conduit 730, they are mixed together, which initiates curing. Distal end 731 of mixing conduit 730 can be configured to achieve a variety of delivery techniques including, for example, extrusion delivery or spray delivery. Moreover, in embodiments that employ a spray delivery technique, distal end 731 of mixing conduit 730 can be configured to deliver the mixture in a variety of spray patterns including, for example, a shower pattern spray, a fan pattern spray, a misting spray, a jet spray, or other spray pattern. Distal end 731 of mixing conduit 730 can alternatively be configured for attachment to a nozzle (not shown), which can itself be configured to achieve a desired manner of extrusion or spray delivery. After the mixture exits distal end 731 of mixing conduit 730, the mixture is positioned for curing. In one preferred embodiment, the period of time following mixing necessary for the mixture to cure is from about 1 to about 30 minutes. In another embodiment the period is from about 2 to about 10 minutes.

Figure 10:
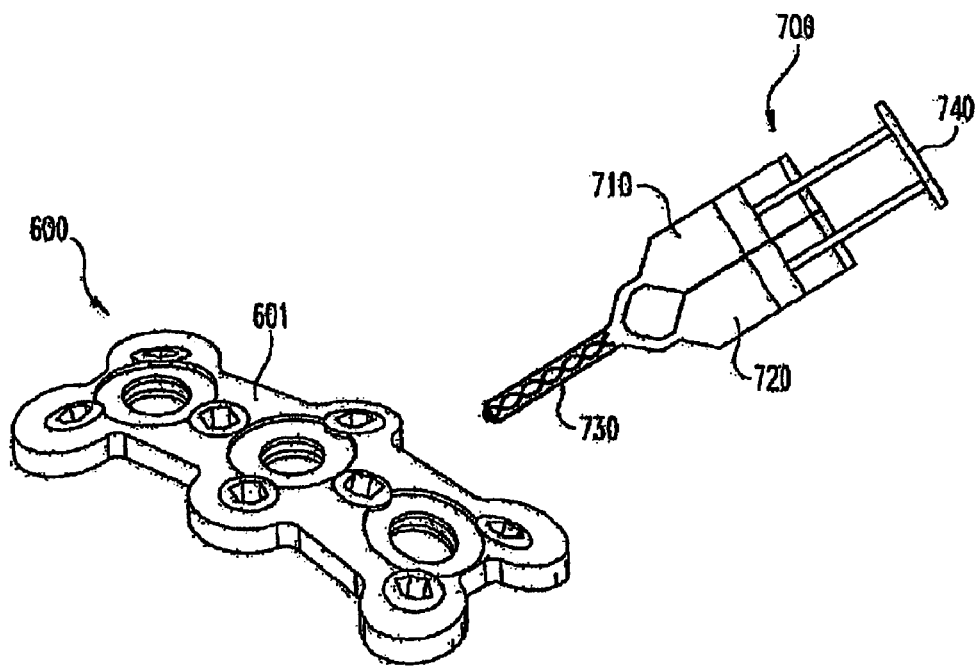
FIG. 10 is a perspective view of a bone plate/screw construct embodiment and a side elevation view of a material delivery device.

Referring now to FIG. 10, two-level anterior cervical plate 601 is implanted surgically using methods known in the art. For example, two-level anterior cervical plate 601 can be implanted for fixation of a C4-C6 level vertebral motion segment. A two-part self-curing mixture is delivered from delivery device 700 onto soft tissue-facing surfaces of plate/screw construct 600. In particularly preferred embodiments, the self-curing mixture is positioned to cover the upper and side surfaces of plate 601 and exposed surfaces of bone screw heads used to affix plate 601 to the vertebrae. The self-curing mixture is then allowed to cure or set up to form a coating before allowing the coating to come into contact with surrounding tissues and the patient's esophagus prior to closing the surgical site. In the embodiment shown in FIG. 10, delivery device 700 is a static mixer that includes first and second chambers 710, 720 in which the separate parts of the two-part self-curing mixture are contained up to the time of extrusion. When plate/screw construct 600 is in position, the two parts can be mixed and delivered to the desired surface or surfaces of construct 600 from delivery device 700. As the materials pass through mixing portion 730, they are mixed together, which initiates curing. After the mixture exits distal end 731 of mixing portion 730, the mixture is formed into position for curing. The present application also contemplates the use of a delivery device that is configured to mix three or more materials at the time of delivery. For example, in addition to a two-part, self-curing mixture, one might wish to also mix a therapeutic agent into the curable composition. This can be achieved by utilizing a three-chamber delivery device (not shown) similar to the two-chamber device depicted in FIGS. 9 and 10, or having other configurations as would occur to one of ordinary skill in the art.

In an alternate embodiment, the flowable, curable material is a single-phase material that is cured by means other than mixing. For example, the material can include cure initiators that are activated by application of radiation or other initiating means such as, for example, moisture, body heat, light or the like. In such an embodiment, the material can be applied using a wide variety of delivery means, including syringe-type delivery devices with a single chamber. A single-phase material can alternatively be delivered using a static mixer such as that depicted in FIGS. 9 and 10 in the manner described above. This may be desirable, for example, in instances where it is desired to produce a coating having a second phase or a coating having a therapeutic agent entrained therein, in which cases such second material can be mixed into the flowable, curable material prior to curing.

In further embodiments of the present application, a therapeutic agent, such as, for example, a drug or bioactive agent, is included in the coating to impart biological properties to the surface of the implant. For example, the therapeutic agent can be selected from the group consisting of analgesic compounds, anesthetics, antibacterial compounds, antibiotics, antibodies, antifungal compounds, anti-inflammatories, antiparasitic compounds, antiviral compounds, anticancer compounds, carbohydrates, cells, cytokines, drugs, genetic agents, enzyme inhibitors, hormones, steroids, glucocorticosteroids, growth factors, immunoglobulins, immunomodulators, lipoproteins, minerals, neuroleptics, nutritional supplements, oligonucleotides, organic polymers, peptides, polysaccharides, proteins, proteoglycans, radiocontrast media, toxins, tumoricidal compounds, tumorstatic compounds, and vitamins. In embodiments in which the coating is composed of a hydrogel, the therapeutic agent is releasable over time as water diffuses into and out of the hydrogel coating. In other embodiments, the coating is partially or completely bioresorbable. When a bioresorbable coating is used, the coating can be engineered to be degraded and absorbed at particular rates by selecting the ratios of the bioresorbable regions to the non-biodegradable regions as well as by controlling the degree of crosslinking and the molecular weight thereof. Thus, when a bioresorbable coating is used together with a therapeutic agent, the coating is operable to deliver controlled quantities of a therapeutic agent to the implant site in the body as the coating is bioresorbed. Examples of bioresorbable materials that can be employed include polylactide, polyglycolide, poly(lactide-co-glycolide), poly(dioxanone), poly(.epsilon.-caprolactone), poly (hydroxylbutyrate), poly(hydroxylvalerate), tyrosine-based polycarbonate, polypropylene fumarate and combinations thereof.

The therapeutic agent can comprise a wide variety of drugs and/or bioactive agents provided that it does not interfere with the desired characteristics and functions of the coating. Examples of suitable drugs or bioactive agents include, for example, without limitation, thrombo-resistant agents, anti-adhesion agents, antibiotic agents, anti-tumor agents, anti-viral agents, anti-fungal agents, anti-angiogenic agents, angiogenic agents, anti-inflammatory agents, anti-cytokines, analgesics, anesthetics, steroids, bacteriostatic compounds, growth factors, nutrients, vitamins, cell cycle regulating agents, their homologs, derivatives, fragments, pharmaceutical salts and combinations thereof. Useful thrombo-resistant agents can include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof. Useful antibiotics can include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof. Useful anti-tumor agents can include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof. Useful anti-viral agents can include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof. The therapeutic agents specifically identified above are provided for example only and a wide variety of other agents known in the art can be selected for use in a coating instead of, or in addition to, one or more of those identified above.

As will be appreciated by a person skilled in the art, the present application includes a wide variety of forms, aspects and embodiments. In one aspect, the present application provides a method for making a spinal implant device having at least one soft tissue-contacting surface that includes (1) providing a load-bearing spinal implant device having at least one soft tissue-facing surface; and (2) applying to the soft tissue-facing surface a coating operable for extended contact with soft tissue in vivo. The load-bearing component can be, for example, an interspinous process spacer, a rigid spinal rod, a flexible spinal rod, a spinal tether, a bone screw, a bone anchor, an anterior spinal fixation plate, a lateral spinal fixation plate, a prosthetic disc nucleus and a disc prosthesis. The coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating. In one embodiment, the coating is compliant and capable of deformation.

The coating can have a variety of forms and can be composed of a variety of materials. In one embodiment, the coating has a thickness of between about 1 and about 500 microns. In another embodiment, the coating has a thickness of between about 10 and about 250 microns. The coating can be composed of a nonbioresorbable material, a bioresorbable material or a semi-resorbable material. In one embodiment the coating comprises a xerogel or a hydrogel. The hydrogel can be, for example, a polyvinyl alcohol, a polyacrylic acid, a polyarylamide, a poly(acrylonitrile-acrylic acid), a polyurethane, a polyethylene glycol, a poly(N-vinyl-2-pyrrolidone), a gelatin, a collagen, a polysaccharide, a cellulose, and combinations thereof. In one embodiment, the hydrogel has a water content when fully hydrated of at least 25% by weight. In another embodiment, the hydrogel has a water content when fully hydrated of at least 50% by weight. The coating can also include a therapeutic agent. Exemplary therapeutic agents that can be included in the coating include, for example, a thrombo-resistant agent, an anti-adhesion agent, an antibiotic agent, an anti-tumor agent, an anti-viral agent, an anti-fungal agent, an anti-angiogenic agent, an angiogenic agent, an anti-inflammatory agent, an anti-cytokine, an analgesic, an anesthetic, a steroid, a bacteriostatic compound, a growth factor, a nutrient, a vitamin, a cell cycle regulating agent, a homolog, derivative, fragment, pharmaceutical salt thereof and combinations thereof.

In one manner of practicing the method, the coating is adhered to the soft tissue-facing surface of the load-bearing component. The coating can be adhered to the soft tissue-facing surface of the load-bearing component, for example, by covalent bonding, ionic bonding, physical attachment or a combination thereof. In one manner of applying the coating to the soft tissue-facing surface, the soft tissue-facing surface is coated with a hydrated coating material, and the material is then dried to provide a dehydrated coating. In another manner of applying the coating to the soft tissue-facing surface, the soft tissue-facing surface is coated with a curable material, and the material is then cured to provide a coating. In yet another manner of applying the coating to the soft tissue-facing surface, a sheet of coating material is adhered to the soft tissue-facing surface. The sheet can have an adhesive layer is adhered to at least a portion of said sheet of coating material, the adhesive layer effective to attach the coating material to the soft tissue-facing surface to provide a coating.

In another aspect, the present application provides a load-bearing spinal implant device that includes a load-bearing component defining at least one soft tissue-facing surface and a coating affixed to the soft tissue-facing surface, the coating operable for extended contact with soft tissue in vivo. The coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating. In one embodiment, the load-bearing component also defines at least one engaging surface operable to contact bone, another implant device or another implant device component, and the engaging surface is substantially free from the coating. In another embodiment, the coating comprises a xerogel coating, and the device is contained in a package in sterile form.

Another aspect of the present application is a method for achieving immobilization or stabilization of a vertebral motion segment that includes (1) providing a load-bearing prosthetic spinal implant device including a load-bearing component defining at least one soft tissue-facing surface and a coating affixed to the soft tissue-facing surface, the coating operable for extended contact with soft tissue in vivo; and (2) surgically affixing the device to a first vertebrae and a second vertebrae of the motion segment. The coating is operable to define an interface with the soft tissue that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating. In one manner of practicing this method, the coating is a xerogel or a partially-hydrated hydrogel and, after said affixing, the coating absorbs water to become hydrated or more fully hydrated.

In yet another aspect, the application provides a method for achieving immobilization or stabilization of a vertebral motion segment that includes (1) providing a load-bearing prosthetic spinal implant device defining at least one soft tissue-facing surface; (2) preparing a surgical site by surgically exposing a vertebral motion segment in need of immobilization or stabilization; (3) surgically affixing the device to a first vertebrae and a second vertebrae of the motion segment; and (4) after said affixing, applying to the soft tissue-facing surface a flowable, curable coating material operable to cure in situ to form a coating effective for extended contact with soft tissue in vivo. The coating is operable to define an interface with the soft tissue that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating. In one embodiment, the method includes allowing the coating to cure before closing the surgical site. In another embodiment, the curable coating material is operable to undergo a transition from a flowable or malleable condition to a non-flowable or non-malleable condition upon curing. Curing can be achieved, for example, by physical means, chemical means or radiation means. Examples of curable coating materials that can be used include silicone, polyurethane, epoxy, polymethylmethacrylate, cyanoacrylate, polyvinyl alcohol hydrogel, polyethylene glycol and the like. In one embodiment, the curable coating material is a two-part self-curing material mixture. Such a material can be applied using a delivery device effective to mix the two-part self-curing material at the time it is applied to the soft tissue-facing surface.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present application and is not intended to limit the present invention in any way to such theory, mechanism of operation, proof, or finding. In reading the claims, words such as the word "a," the word "an," the words "at least one," and the words "at least a portion" are not intended to limit the claims to only one item unless specifically stated to the contrary. Further, when the language "at least a portion" and/or "a portion" is used, the claims may include a portion and/or the entire item unless specifically stated to the contrary. In addition, the various procedures, techniques, and operations may be altered, rearranged, substituted, deleted, duplicated, or combined as would occur to those skilled in the art. Further, any U.S. Patent, pending U.S. patent application Publication or other publication cited herein is incorporated herein by reference in its entirety as if each individual publication, patent, or patent application was specifically and individually indicated to be incorporated by reference and set forth in its entirety herein.

Any reference to a specific direction, for example, references to up, upper, down, lower, and the like, is to be understood for illustrative purposes only or to better identify or distinguish various components from one another. Unless specifically identified to the contrary, all terms used herein are used to include their normal and customary terminology. Further, while various embodiments of devices having specific components and structures are described and illustrated herein, it is to be understood that any selected embodiment can include one or more of the specific components and/or structures described for another embodiment where possible.

What is claimed is:

1. A method for making a spinal implant device having at least one soft tissue-contacting surface, comprising:
   providing a load-bearing spinal implant device having at least one soft tissue-facing surface; and
   applying to the soft tissue-facing surface a coating operable for extended contact with soft tissue in vivo;
   wherein the coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating, and wherein the coating comprises a xerogel or a hydrogel; and
   surgically affixing the device to the spinal column: and
   wherein, after said affixing, the coating absorbs water to become hydrated or more fully hydrated.

2. The method in accordance with claim 1 wherein the coating comprises a xerogel.

3. The method in accordance with claim 1 wherein the coating comprises a hydrogel selected form the group consisting of a polyvinyl alcohol, a polyacrylic acid, a polyarylamide, a poly(acrylonitrile-acrylic acid), a polyurethane, a polyethylene glycol, a poly(N-vinyl-2-pyrrolidone), a gelatin, a collagen, a polysaccharide, a cellulose, and combinations thereof.

4. The method in accordance with claim 1 wherein the coating comprises a hydrogel having a water content when fully hydrated of at least 25% by weight.

5. The method in accordance with claim 1 wherein the coating has a thickness of between about 1 and about 500 microns.

6. The method in accordance with claim 1 wherein the coating is adhered to the soft tissue-facing surface of the load-bearing component.

7. The method in accordance with claim 6 wherein the coating is adhered to the soft tissue-facing surface of the load-bearing component by covalent bonding, ionic bonding, physical attachment or a combination thereof.

8. The method in accordance with claim 1 wherein said applying comprises coating the soft tissue-facing surface with a hydrated coating material, and drying the material to provide a dehydrated coating.

9. The method in accordance with claim 1 wherein said applying comprises coating the soft tissue-facing surface with a curable material, and curing the material to provide a coating.

10. The method in accordance with claim 1 wherein the load-bearing component is selected from the group consisting of an interspinous process spacer, a rigid spinal rod, a flexible spinal rod, a spinal tether, a bone screw, a bone anchor, an anterior spinal fixation plate, a lateral spinal fixation plate, a prosthetic disc nucleus and a disc prosthesis.

11. The method in accordance with claim 1 wherein said applying comprises providing a sheet of coating material and adhering the sheet to the soft tissue-facing surface.

12. The method in accordance with claim 11 wherein an adhesive layer is adhered to at least a portion of said sheet of coating material, and wherein said adhesive layer is effective to attach said coating material to said soft tissue-facing surface to provide a coating.

13. The method in accordance with claim 1 wherein the load-bearing spinal implant device also defines at least one bone-engaging surface that is positioned in contact with bone; and
wherein the bone-engaging surface is substantially free from the coating.

14. A load-bearing spinal implant device, comprising:
a load-bearing component defining at least one soft tissue-facing surface; and
a coating affixed to the soft tissue-facing surface, the coating operable for extended contact with soft tissue in vivo;
wherein the coating is operable to define an interface with the soft tissue that exhibits a feature selected from the group consisting of reduced friction, reduced tissue irritation, reduced adhesion, reduced inflammation, reduced incidence of infection and reduced pain, relative to the soft tissue-facing surface of the load-bearing device in the absence of the coating, and wherein the coating comprises a xerogel or a hydrogel; and
surgically affixing the device to the spinal column; and
wherein, after said affixing, the coating absorbs water to become hydrated or more fully hydrated.

15. The device in accordance with claim 14 wherein the load-bearing component also defines at least one engaging surface operable to contact bone, another implant device or another implant device component; and wherein said engaging surface is substantially free from said coating.

16. The device in accordance with claim 14 wherein said coating comprises a therapeutic agent.

17. The device in accordance with claim 16 wherein said therapeutic agent is selected from the group consisting of a thrombo-resistant agent, an anti-adhesion agent, an antibiotic agent, an anti-tumor agent, an anti-viral agent, an anti-fungal agent, an anti-angiogenic agent, an angiogenic agent, an anti-inflammatory agent, an anti-cytokine, an analgesic, an anesthetic, a steroid, a bacteriostatic compound, a growth factor, a nutrient, a vitamin, a cell cycle regulating agent, a homolog, derivative, fragment, pharmaceutical salt thereof and combinations thereof.

18. The device in accordance with claim 14 wherein the coating is composed of a material selected from the group consisting of a nonbioresorbable material, a bioresorbable material and a semi-resorbable material.

19. The device in accordance with claim 14 wherein the load-bearing component is selected from the group consisting of an interspinous process spacer, a rigid spinal rod, a flexible spinal rod, a spinal tether, a bone screw, a bone anchor, an anterior spinal fixation plate, a lateral spinal fixation plate, a prosthetic disc nucleus and a disc prosthesis.

20. The device in accordance with claim 14 wherein the device is contained in a package in sterile form.

21. The device in accordance with claim 14 wherein the load-bearing component also defines at least one bone-engaging surface that is positioned in contact with bone; and
wherein said bone-engaging surface is substantially free from said coating.

22. A method for achieving immobilization or stabilization of a vertebral motion segment, comprising;
providing a load-bearing prosthetic spinal implant device including a load-bearing component defining at least one soft tissue-facing surface and a coating affixed to the soft tissue-facing surface, the coating operable for extended contact with soft tissue in vivo, and wherein the coating comprises a xerogel or a hydrogel; and
surgically affixing the device to a first vertebrae and a second vertebrae of the motion segment;
forming an interface between the soft tissue and the coating that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating; and
wherein, after said affixing, the coating absorbs water to become hydrated or more fully hydrated.

23. The method in accordance with claim 22 wherein the load-bearing component also defines at least one bone-engaging surface that is positioned in contact with bone; and
wherein the bone-engaging surface is substantially free from the coating.

24. A method for achieving immobilization or stabilization of a vertebral motion segment, comprising:
providing a spinal implant device having at least one soft tissue-facing surface;
preparing a surgical site by surgically exposing a vertebral motion segment in need of immobilization or stabilization;
surgically affixing the device to a first vertebra and a second vertebra of the motion segment; and
after said affixing, applying to the soft tissue-facing surface a flowable, curable coating material operable to cure in situ to form a coating effective for extended contact with soft tissue in vivo, wherein the curable coating material is selected from the group consisting of silicone, polyurethane, epoxy, polymethylmethacrylate, cyanoacrylate, polyvinyl alcohol hydrogel and polyethylene glycol;

forming an interface between the soft tissue and the coating that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating.

25. The method in accordance with claim 24, further comprising allowing said coating to cure before closing the surgical site.

26. The method in accordance with claim 24 wherein the curable coating material comprises a xerogel or a hydrogel.

27. The method in accordance with claim 24 wherein the spinal implant device also defines at least one bone-engaging surface that is positioned in contact with bone; and wherein the bone-engaging surface is substantially free from the coating.

28. A method for achieving immobilization or stabilization of a vertebral motion segment, comprising:

providing a spinal implant device having at least one soft tissue-facing surface;

preparing a surgical site by surgically exposing a vertebral motion segment in need of immobilization or stabilization;

surgically affixing the device to a first vertebra and a second vertebra of the motion segment; and after said affixing, applying to the soft tissue-facing surface a flowable, curable coating material operable to cure in situ to form a coating effective for extended contact with soft tissue in vivo;

wherein the coating is operable to define an interface with the soft tissue that exhibits a feature selected from the group consisting of reduced friction, reduced tissue irritation, reduced adhesion, reduced inflammation, reduced incidence of infection and reduced pain, relative to an interface between the soft tissue and the soft tissue-facing surface of the load-bearing device in the absence of the coating;

wherein the curable coating material is a two-part self-curing mixture; and wherein the curable coating material is applied using a delivery device effective to mix the two-part self-curing silicone material at the time it is applied to the surface.

* * * * *